United States Patent
Espinosa et al.

(10) Patent No.: US 9,423,399 B2
(45) Date of Patent: Aug. 23, 2016

(54) LATERAL FLOW ASSAYS FOR TAGGED ANALYTES

(71) Applicant: Clontech Laboratories, Inc., Mountain View, CA (US)

(72) Inventors: Eric Espinosa, Mountain View, CA (US); Andrew Farmer, Mountain View, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 604 days.

(21) Appl. No.: 14/023,266

(22) Filed: Sep. 10, 2013

(65) Prior Publication Data

US 2014/0093865 A1     Apr. 3, 2014

Related U.S. Application Data

(60) Provisional application No. 61/707,076, filed on Sep. 28, 2012.

(51) Int. Cl.
*G01N 33/558* (2006.01)

(52) U.S. Cl.
CPC .................................. *G01N 33/558* (2013.01)

(58) Field of Classification Search
None
See application file for complete search history.

(56) References Cited

U.S. PATENT DOCUMENTS

| | | | |
|---|---|---|---|
| 5,424,220 A * | 6/1995 | Goerlach-Graw ... | G01N 33/558 422/401 |
| 6,656,744 B2 | 12/2003 | Pronovost et al. | |
| 7,749,776 B2 | 7/2010 | Lamotte | |
| 7,790,400 B2 | 9/2010 | Jehanli et al. | |
| 7,888,040 B2 | 2/2011 | Jehanli | |
| 2004/0110167 A1 | 6/2004 | Gerdes et al. | |
| 2005/0227275 A1 | 10/2005 | Jung et al. | |
| 2006/0160078 A1 | 7/2006 | Cardy et al. | |
| 2009/0047673 A1 | 2/2009 | Cary | |
| 2009/0305290 A1 | 12/2009 | Sambursky et al. | |
| 2010/0136531 A1 | 6/2010 | Garthwaite et al. | |

OTHER PUBLICATIONS

Wang S. et al., "Lateral Flow Colloidal Gold-Based Immunoassay for Pesticide", Methods Mol Biol., 2009, 504:237-252.
Song C. et al., "Development of a Lateral Flow Colloidal Gold Immunoassay Strip for the Rapid Detection of Olaquindox Residues", J Agric Food Chem., Sep. 14, 2011, 59(17):9319-9326.
Tripathi V. et al, "A competitive immunochromatographic strip assay for 17-a-hydroxy progesterone using colloidal gold nanoparticles", Clinica Chimca Acta., Jan. 18, 2012, 413(1-2):262-268.
Tang Y. et al., "Development of a Lateral Flow Immunoassay (LFA) Strip for the Rapid Detection of 1-Aminohydantoin in Meat Samples", J Food Sci., Aug. 2011, 76(6):T138-43.
Lu S.Y. et al., A screening lateral flow immunochromatographic assay for on-site detection of okadaic acid in shellfish products', Anal Biochem., Mar. 15, 2012, 422(2):59-65.

* cited by examiner

*Primary Examiner* — Chris L Chin
(74) *Attorney, Agent, or Firm* — Bret E. Field; Bozicevic, Field & Francis LLP

(57) ABSTRACT

Methods of determining whether an analyte is present in a sample using a competitive assay are provided. Aspects of the methods include employing a competitor that provides for the obtainment of signal which is directly proportional to the amount of analyte in the sample. Also provided are devices and kits that find use in practicing the methods described herein.

12 Claims, 7 Drawing Sheets

LATERAL FLOW ASSAYS FOR TAGGED ANALYTES

CROSS REFERENCE TO RELATED APPLICATIONS

Pursuant to 35 U.S.C. §119 (e), this application claims priority to the filing date of the U.S. Provisional Patent Application Ser. No. 61/707,076, filed Sep. 28, 2012; the disclosure of which is herein incorporated by reference.

INTRODUCTION

Various lateral flow assay test strips are utilized to test for the presence of, absence of or quantity of an analyte in a biological sample for diagnostic purposes. Conventional lateral flow test strips feature a solid support on which a sample receiving area and the target capture zones are supported. The solid support material is one which is capable of supporting the sample receiving area and target capture zones and providing for the capillary flow of sample out from the sample receiving area to the target capture zones when the lateral flow test strip is exposed to an appropriate solvent or buffer, which acts as a carrier liquid for the sample.

Traditional lateral flow test strips contain one or more target capture lines. These capture lines are located on the strip parallel with the sample receiving area such that the flow of the sample from a sample receiving area sequentially contacts each of the capture lines. During use, sample aliquots are deposited onto a sample receiving area of the lateral flow test strip. Solvent or carrier liquid flows across the strip and carries the sample material across the target capture zones toward an absorbent pad located at the end of the test strip.

Conventional lateral flow test strips function on the principle of either a sandwich assay format or a competitive assay format. In traditional sandwich assay formats, the detected signal is directly proportional to the amount of analyte present in the sample such that increasing amounts of analyte lead to increasing signal intensity. In traditional competitive assay formats, the detected signal has an inverse relationship with the amount of analyte present such that increasing amounts of analyte lead to decreasing signal intensity.

SUMMARY

Methods of determining whether an analyte is present in a sample using a competitive assay are provided. Aspects of the methods include employing a competitor that provides for the obtainment of signal which is directly proportional to the amount of analyte in the sample. Also provided are devices and kits that find use in practicing the methods described herein.

BRIEF DESCRIPTION OF THE FIGURES

FIGS. 1B and 1C illustrate negative (1B) and positive (1C) results obtained with the device illustrated in 1A.

DETAILED DESCRIPTION

Figure 1:
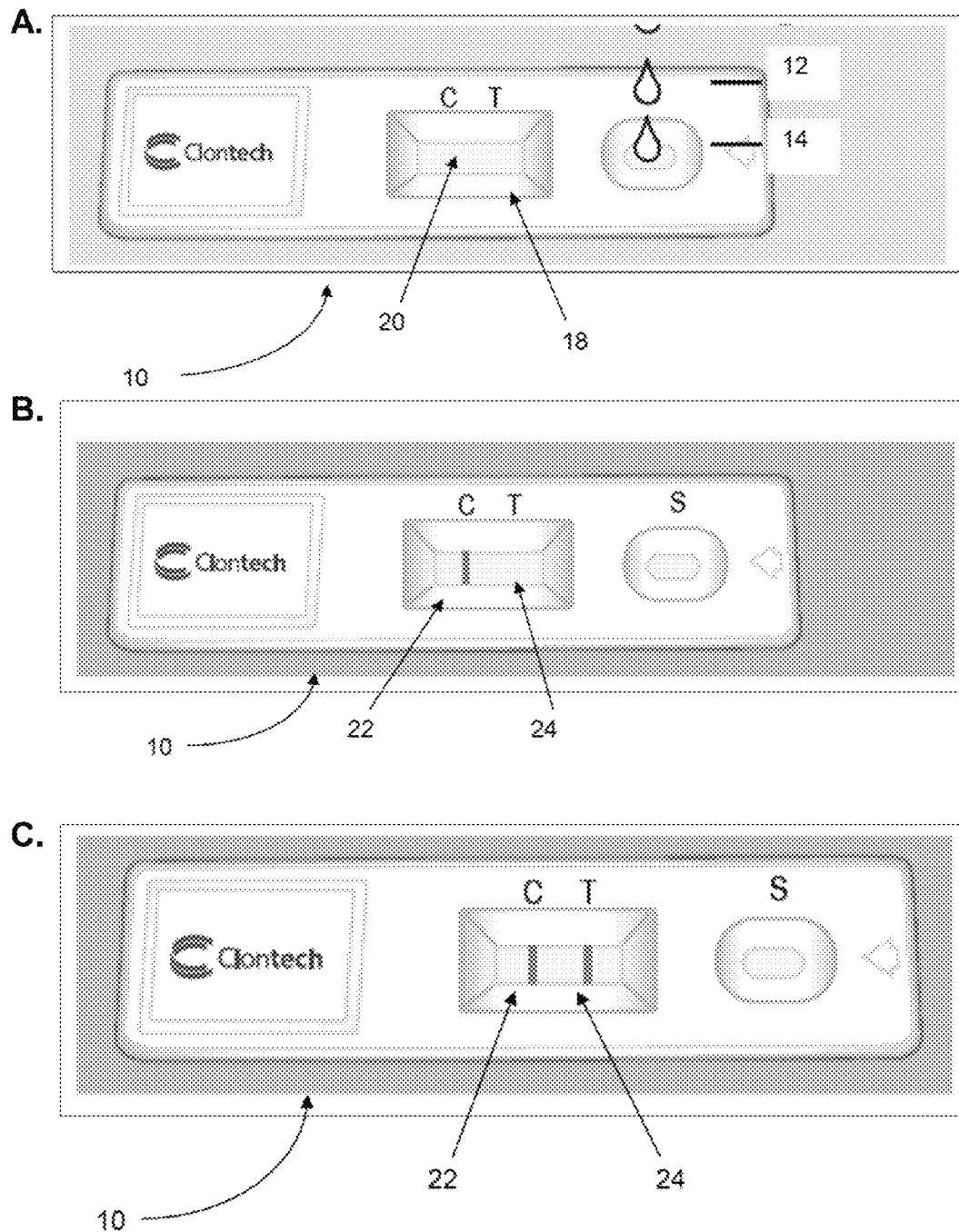
FIG. 1 shows a depiction of a lateral flow assay device according to an embodiment of the invention (1A).

Methods of determining whether an analyte is present in a sample using a competitive assay are provided. Aspects of the methods include employing a competitor that provides for the obtainment of signal which is directly proportional to the amount of analyte in the sample. Also provided are devices and kits that find use in practicing the methods described herein.

Before the present invention is described in greater detail, it is to be understood that this invention is not limited to particular embodiments described, as such may, of course, vary. The invention encompasses various alternatives, modifications, and equivalents, as will be appreciated by those of skill in the art. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

Any publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Methods and Devices

Aspects of the invention include methods of using a lateral flow assay device to determine whether an analyte is present in a sample. As such, methods of the invention are methods of detecting the presence of an analyte in a sample, where the detection may be qualitative or quantitative, e.g., as described in greater detail below. In other words, the methods are methods of identifying that a target analyte is present in a sample. In some embodiments, the methods include determining whether an analyte is present in a sample. In some embodiments, the methods include determining a quantitative measure of the amount of analyte in a sample. In some embodiments, the methods include determining whether an analyte is present in a sample above a predetermined threshold.

Aspects of the methods include applying a volume of a sample to a "lateral flow assay device" (also referred to herein as a "test lateral flow assay device" or "a lateral flow assay test strip"). As the assay device is a "lateral flow" assay device, it is configured to receive a sample of interest at a sample receiving region and to provide for the sample to move laterally, e.g., via wicking, through a bibulous material (i.e., bibulous member) by capillary action to a detection region, such that the sample is wicked laterally through the bibulous member from the sample receiving region to the detection region.

Assays of the invention are competitive assays in which the signal obtained from the assay is directly proportional to the amount of analyte that is present in the sample being assayed. By directly proportional is meant that the signal provided by the assay becomes larger or smaller when the as the amount of analyte in the sample becomes larger or smaller. Therefore, as the amount of analyte increases the detected signal intensity provided by the assay increases. Conversely, as the amount of analyte decreases in the sample, the detected signal intensity provided by the assay also decreases. Thus, the intensity of the detected signal is directly proportional to the amount of analyte present in the sample.

Competitive assays of the invention are assays which employ competition or competitive binding. The terms "competition" and "competitive binding" are used to describe a system in which a target analyte and a competitor molecule (also referred to herein as a "competitor," described in more detail below), compete for binding to a capture probe component of the assay, e.g., one that is immobilized at some portion of a test lateral flow assay device, e.g., in the sample receiving region, such as described in greater detail below.

Aspects of the invention include the use of a competitor. A "competitor" is a molecule that both: (1) competes with the analyte of interest for binding to a first capture probe; and (2) specifically binds to a detection capture probe of the detection region, e.g., where these regions and probes are described in greater detail below. A competitor includes a first binding pair member (e.g., moiety that specifically binds to another moiety (such as an epitope that is bound by an antibody or binding fragment thereof), where "binding pair member" is further defined below) that specifically binds to a first capture probe. In some embodiments, the first binding pair member also specifically binds to a detection capture probe. In some embodiments, a competitor includes two or more binding pair members. In some embodiments, the first binding pair member of the competitor is identical to another binding pair member of the competitor. In some embodiments, each of the two or more binding pair members of the competitor is different.

In some embodiments, the competitor includes two binding pair members, where the competitor specifically binds to a first capture probe via the first binding pair member and to a detection capture probe via the second binding pair member. In some embodiments, the competitor includes three binding pair members, where the competitor specifically binds to a first capture probe via the first binding pair member, to a detection capture probe via the second binding pair member, and to a reporter (described below) via the third binding pair member.

A competitor can be any molecule that that competes with an analyte of interest for binding to the first capture probe of the lateral flow assay device (described in greater detail below). As such, competitors will include a moiety, e.g., epitope, that specifically binds to a first capture probe of the device, such as further described below in the context of specific binding pair members. The moiety may be one that is common to a moiety of present on the analyte of interest, or different from the analyte moiety that specifically binds to the first capture probe, so long as capture probe specific binding moieties of the competitor and target analyte have substantially the same binding affinity and avidity to the first capture probes so as to effectively compete for binding to the first capture probe. Competitors can vary in molecular weight, ranging in some instances from 500 to 500,000 daltons, such as 500 to 250,000 daltons, e.g., 500 to 150,000 daltons. 500 to >150,000 daltons. Competitors may vary, and in some instances may be organic molecules, including biomolecules, e.g., polypeptides (such as antibodies and binding fragments thereof, fusion proteins (including proteins tagged with a proteinaceous tag, such as a poly-his tag, FLAG epitope, etc.), nucleic acids, carbohydrates, etc.

In some embodiments, the competitor includes a label moiety. A "label moiety" is any moiety that provides for signal detection and may vary widely depending on the particular nature of the lateral flow assay. Label moieties of interest include both directly (e.g., a gold particle) and indirectly (e.g., a binding pair member) detectable labels. Any of the components described herein may include a label moiety. Suitable detectable (directly or indirectly) label moieties for use in the methods described herein include any moiety that is detectable by spectroscopic, photochemical, biochemical, immunochemical, electrical, optical, chemical, or other means. For example, suitable labels include biotin for staining with labeled streptavidin conjugate, a fluorescent dye (e.g., fluorescein, Texas red, rhodamine, green fluorescent protein, and the like), a radiolabel (e.g., $^3$H, $^{125}$I, $^{35}$S, $^{14}$C, or $^{32}$P), an enzyme (e.g., peroxidase, alkaline phosphatase, galactosidase, and others commonly used in an ELISA), a fluorescent protein (e.g., green fluorescent protein, red fluorescent protein, yellow fluorescent protein, and the like), a metal label, a colorimetric label, a binding pair member, and the like. Any binding pair member can be suitable for use as an indirectly detectable label moiety.

Metal labels of interest include metal particles (e.g., gold) that can be directly detected and/or indirectly detected. Metal labels can also be metal particles provided in a colloid (e.g., colloidal gold). Colorometric labels (e.g., colored glass, colored plastic, e.g., polystyrene, polypropylene, latex beads, and the like) are labels that can be seen visibly without the aid of laboratory equipment. Patents that describe the use of such labels include U.S. Pat. Nos. 3,817,837; 3,850,752; 3,939, 350; 3,996,345; 4,277,437; 4,275,149; and 4,366,241. See also Handbook of Fluorescent Probes and Research Chemicals (6th Ed., Molecular Probes, Inc., Eugene Oreg.). Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

In further describing various aspects of the invention, embodiments of lateral flow assay devices finding use in methods of the invention are reviewed first in greater detail, followed by a review of various embodiments of the methods using the devices.

Devices

As mentioned above, lateral flow assay devices employed in methods of the invention are configured to provide for lateral flow of a sample from a sample receiving region to a detection region. In some instances, the devices include a bibulous member. A bibulous member is one that readily absorbs liquid and provides for liquid flow through the member. "Bibulous members" employed in devices described herein may be fabricated from any convenient bibulous material. Examples of bibulous materials include, but are not limited to: organic or inorganic polymers, and natural and synthetic polymers. More specific examples of suitable solid supports include, without limitation, glass fiber, cellulose, nylon, cross-linked dextran, various chromatographic papers and nitrocellulose.

While the bibulous member and overall configuration of a subject test lateral flow assay device may vary, in certain embodiments the bibulous member can have a strip configuration. Where the bibulous material is configured as a strip, the bibulous member can have a length that is longer than its width. While any practical configuration may be employed, in some instances the length is longer than the width by 1.5 fold or more, such as 2-fold or more, e.g., 10 fold or more, including 20-fold or more. In some instances, the length of the bibulous member ranges from 0.5 to 20 cm, such as 1.0 to 15 cm, e.g., 2.0 to 10 cm, while the width ranges 0.1 to 5.0 cm, such as 0.5 to 2.5 cm, e.g., 1 to 2 cm. The thickness of the bibulous member may also vary, ranging in some instances from 0.01 to 0.05 cm, such as 0.1 to 0.4 cm, e.g., 0.1 to 0.25 cm.

Optionally, the test lateral flow assay device can include an absorbent pad downstream from the detection region and any control region, e.g., at the end distal from the sample receiving region, where the absorbent pad is configured to absorb fluid and reagents present therein that have flowed through the bibulous member. While the configuration of the absorbent pad may vary, in some instances it is configured to absorb a volume of liquid that is substantially the same as the volume of sample that is applied to the sample receiving region during use.

A test lateral flow assay device includes a sample receiving region and a detection region. A test lateral flow assay device can also include a control region. The "sample receiving region" can simply be a first region of the bibulous member, e.g., positioned closer to one end of the bibulous member. Alternatively, the sample receiving region may be distinct from the bibulous member, but configured to provide for fluid communication of sample into the bibulous member upon application of sample to the sample receiving region. The sample receiving region may be configured to receive samples of varying volumes, where in some instances the sample receiving region is configured to receive a sample having a volume ranging from 0.1 to 1000 µl such as 5 to 20 µl and including 50 to 200 µl.

In some instances, the sample receiving region may include a metering device configured to meter a specific amount of sample into the bibulous member. Examples of metering devices include those described in United States Published Patent Application Nos.: 20080145272; 20070134810; 20060008847; and 20050227370.

The sample receiving region is a region that includes a distinct capture probe region. A "capture probe region" or "capture region" is a region that includes an amount of a "capture probe" (also referred to as an "immobilized capture probe;" i.e., a capture probe that is stably associated with the bibulous member in the capture probe region). The size of a sample receiving capture probe region may vary, and in some instances a capture probe region can have an area ranging from 0.01 to 0.5 cm$^2$, such as 0.05 to 0.1 cm$^2$ and including 0.1 to 0.2 cm$^2$. A sample receiving region can include a single capture probe region or two or more different capture probe regions, where each of the two or more different capture probe regions includes a capture probe, where the capture probe in each region can be the same or different. When the sample receiving region includes two or more capture probe regions, the capture probe regions can be distinct from each other or overlapping, as desired. (Two or more distinct capture probe regions may be present, e.g., in devices configured for use in multiplex assays).

A "capture probe" is an immobilized molecule that specifically binds to another molecule (e.g., an analyte of interest, a competitor, and the like). The terms "binds," "binds to," "binding," and the like, as used herein (e.g., with reference to capture probes, binding pair members, and the like) refer to a non-covalent interaction between entities (e.g., between a metal ion affinity peptide and a metal ion, between an antibody and an antigen, and the like). The terms "specific binding," "specifically binds," and the like, refer to the preferential binding to a molecule (e.g., one binding pair member to the other binding pair member of the same binding pair, a capture probe to an analyte, a capture probe to a competitor, an immobilized control agent to a mobile control binding agent, etc.) relative to other molecules or moieties in a solution or reaction mixture. In some cases, "specifically binds" refers to preferential binding to one molecule in solution. In some cases, "specifically binds" refers to preferential binding to more than one molecule in solution (e.g., a member of a binding pair can specifically bind to two different molecules in the same solution). For example, a capture probe (described below) of the sample receiving region specifically binds (i.e., preferentially binds) to a subject analyte and to a competitor (defined below), but can only bind one of the two molecules at a time.

"Immobilized" or "stably associated with the bibulous material" means that a molecule (e.g., capture probe, immobilized control agent, etc.) and the bibulous member maintain their position relative to each other in space under the conditions of use, e.g., under the assay conditions. As such, an immobilized capture probe and the bibulous member can be non-covalently or covalently stably associated with each other. Examples of non-covalent association include non-specific adsorption, binding based on electrostatic (e.g., ion-ion pair interactions), Van der Waals forces, hydrophobic interactions, hydrogen bonding interactions, and the like. Examples of covalent binding include covalent bonds formed between a capture probe and a functional group present on the bibulous material.

As mentioned above, a "capture probe," also referred to herein as an "immobilized capture probe," is an immobilized molecule that specifically binds to another molecule (e.g., an analyte of interest, a competitor, and the like). In some embodiments, the affinity between a capture probe and the molecule to which it specifically binds when they are specifically bound to each other in a binding complex is characterized by a $K_D$ (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower Kd.

A variety of different types of specific binding agents may be employed as a capture probe. A capture probe is therefore considered to include a binding pair member (defined below). Specific binding agents that can be used as a capture probe include antibody binding agents, proteins, peptides (e.g., glutathione, epitopes, tags, etc.), haptens, nucleic acids, metal ions (e.g., $Ni^{+2}$, $Co^{+2}$, $Fe^{+3}$, $Al^{+3}$, $Zn^{+2}$, $Cu^{+2}$, etc.), carbohydrates (e.g., amylose, maltose), and the like. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'$_2$ fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

A "binding pair member" is one of a first and a second moiety, wherein the first and the second moiety have a specific binding affinity for each other. Together the first and second moiety can be referred to as a "binding pair," and each moiety (first and second) of the binding pair is therefore a binding pair member. Accordingly, a molecule may be said to include a binding pair member. A molecule may also be said to include two or more binding pair members, each of which can be members of different binding pairs. As mentioned above, in some instances the affinity of a first binding pair member to a second binding pair member of a give binding pair is characterized by a $K_D$ (dissociation constant) of $10^{-5}$ M or less, e.g., $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower Kd.

Suitable binding pairs include, but are not limited to, antigen/antibody pairs. Antigen/antibody pairs may include, for example, but are not limited to natural epitope/antibody pairs (e.g., insulin epitope/anti-insulin), laboratory generated antigen/antibody pairs (e.g., digoxigenin (DIG)/anti-DIG; dinitrophenyl (DNP)/anti-DNP; dansyl-X/anti-dansyl; Fluorescein/anti-fluorescein; lucifer yellow/anti-lucifer yellow; rhodamine/anti-rhodamine, etc), peptide or polypeptide antigen/antibody pairs (e.g., FLAG, histidine tag, hemagglutinin (HA) tag, c-myc tag, glutathione S transferase (GST) tag, protein A, Strep-tag, maltose binding protein (MBP), chitin-binding domain (CBD), S-tag, calmodulin binding protein (CBP), tandem affinity purification (TAP) tag, SF-TAP tag, VSV-G tag, herpes simplex virus (HSV) epitope tag, V5 epitope tag, 6xHN epitope, KT3 epitope [Martin et al., Science, 255:192-194 (1992)], tubulin epitope peptide (Skinner et al., J. Biol. Chem., 266:15163-15166 (1991)], the T7 gene 10 protein peptide tag [Lutz-Freyermuth et al., Proc. Natl. Acad. Sci. USA, 87:6393-6397 (1990)), etc. and the antibodies each thereto), and the like (Brizzard (2008) BioTechniques 44:693-695).

Suitable binding pairs also include, but are not limited to, pairs that are not antigen/antibody pairs, e.g., metal ion affinity peptide/metal ion (e.g., metal ion affinity peptides, e.g., histidine tag, that bind to metal ions such as $Ni^{+2}$, $Co^{+2}$, $Fe^{+3}$, $Al^{+3}$, $Zn^{+2}$, $Cu^{+2}$, and the like.), GST polypeptide/glutathione, Strep-Tactin, MBP/maltose (or amylose), CBD; chitin, Avitag/Avidin, CBP/calmodulin, TAP/calmodulin and/or IgG, SF-TAP/Strep-Tactin, biotin/avidin, biotin/streptavidin, biotin/neutravidin, and the like. A "metal ion affinity peptide" or "metal ion affinity tag" is a peptide that binds preferentially to a metal ion (e.g., $Ni^{+2}$, $Co^{+2}$, $Fe^{+3}$, $Al^{+3}$, $Zn^{+2}$, $Cu^{+2}$, and the like). A "histidine tag" or "histidine-rich affinity peptide" is a metal ion affinity peptide that is rich in histidines (e.g., 6xHis tag, HAT tag, 6xHN tag, and the like). A histidine tag can also specifically bind to an anti-His antibody.

A "capture probe of a sample receiving region," also referred to herein as a "first capture probe," specifically binds to an analyte and also specifically binds to a competitor, but can only bind to one or the other at any given time. The analyte and competitor therefore compete for binding to a first capture probe. In some embodiments, the analyte and competitor compete for binding to the first capture probe because they each include the same binding pair member. In some embodiments, the first capture probe can bind to two or more different binding pair members and the analyte and competitor each include a different binding pair member. For example, in some embodiments, the first capture probe is an immobilized metal ion (e.g., $Ni^{+2}$, $Co^{+2}$, $Fe^{+3}$, $Al^{+3}$, $Zn^{+2}$, $Cu^{+2}$, and the like) that specifically binds to a metal ion affinity peptide. In such a case, the analyte and competitor each include the same or different metal ion affinity peptides, which thereby compete for binding to the capture probe.

In some embodiments, the sample receiving region of the lateral flow assay device includes multiple different capture probes, each of which specifically binds to a different binding pair member. As a non-limiting example, a sample receiving region can contain all or any combination of the following: anti-histidine tag antibody, immobilized metal ions (e.g., $Ni^{+2}$, $Co^{+2}$, $Fe^{+3}$, $Al^{+3}$, $Zn^{+2}$, $Cu^{+2}$), glutathione, maltose, amylose, chitin, avidin, streptavidin, neutravidin, calmodulin, anti-V5 tag antibody, anti-c-myc tag antibody, anti-HA tag antibody, anti-HSV tag antibody, anti-TAP tag antibody, and the like.

In addition to the sample receiving region, a lateral flow assay device further includes a "detection region". A detection region is a region of the bibulous member from which a result may be read during use of the device. The detection region is positioned at some distance downstream from the sample receiving region of the device. By "downstream" is meant the lateral direction that the sample flows by capillary action, i.e., the direction of fluid flow from the sample receiving region. The distance between the sample receiving region and the detection region may vary, ranging in some instances from 0.3 to 15 cm, such as 1 to 15 cm and including 5 to 10 cm, e.g., 1 to 5 cm.

The detection region is a region that includes a distinct detection capture probe region. A detection capture probe region of the detection region is a region that includes an amount of a capture probe of the detection region, also referred to herein as a "detection capture probe." A detection capture probe is immobilized in the detection capture probe region and specifically binds to a competitor. In some embodiments, a detection capture probe specifically binds to the same binding pair member (of the competitor) that is specifically bound by the first capture probe. For example, in some embodiments, the detection capture probe and the first capture probe both specifically bind to the first binding pair member of the competitor. In some embodiments, a detection capture probe specifically binds to a different binding pair member (of the competitor) than is specifically bound by the first capture probe. For example, in some embodiments, the detection capture probe specifically binds to a second binding pair member of the competitor while the first capture probe specifically binds to the first binding pair member of the competitor.

The size of the detection capture probe region may vary, and in some instances the capture probe region can have an area ranging from 0.01 to 0.5 $cm^2$, such as 0.05 to 0.1 $cm^2$ and including 0.1 to 0.2 $cm^2$. A detection capture probe region can have a variety of different configurations, where the configuration can be random or the configuration can have a specific shape such as a line, circle, square, or more complex shape, such as a "+", as desired.

A detection region can include a single detection capture probe region or two or more different capture probe regions, where each of the two or more different capture probe regions includes a capture probe, where the capture probe in each region can be the same (such as is found in a quantitative assay device) or different. Where the detection region includes two or more capture probe regions, the capture probe regions can be distinct from each other or overlapping, as desired.

In some embodiments, the test lateral flow assay device includes a single flow lane linking the sample receiving region to the detection region. In some embodiments, the test lateral flow assay device includes two or more separate sample receiving regions, each having the same capture probe or set of capture probes and each connected with its own detection region. In some embodiments, the test lateral flow assay device includes two or more separate sample receiving regions, each having a different capture probe or set of capture probes and each connected with its own detection region. Accordingly, a given test lateral flow assay device can include two or more distinct flow lanes, each having its own sample receiving region and detection region.

In some embodiments, a competitor (e.g., as described above) is associated with the sample receiving region prior to the addition of sample. In such instances, the sample receiving region of the test lateral flow assay device can therefore be said to include a competitor. In such cases, the competitor is "not immobilized," also referred to as "non-stably associated." "Not immobilized" or "non-stably associated" means that while a molecule (e.g., competitor, mobile control binding agent, reporter, and the like) may be stationary relative to the bibulous member of the test lateral flow assay device prior to the application of sample, upon sample application and sample wicking through the bibulous binding member, the molecule is free to interact with other components of the system (e.g., first capture probe, analyte, competitor, mobile control binding agent, reporter, second capture probe, immobilized control agent, and the like) and can move through the bibulous member by capillary action (i.e., under the bulk fluid flow forces) toward the detection region.

In some embodiments, the lateral flow assay device includes an internal control region. When present, the internal control region is located downstream from the sample receiving region. The internal control region may overlap with the detection region to any degree desired, or may be located upstream or downstream from the detection region, as desired. The internal control region contains a control agent that is immobilized (i.e., an "immobilized control agent"). The immobilized control agent binds specifically to a "mobile control binding agent" (a control binding agent that is not immobilized) to form a control binding pair, e.g., as described in U.S. Pat. No. 6,136,610. In some embodiments, a control binding pair acts as an "internal control", that is, the control against which the analyte measurement results may be compared on the individual test strip. A lateral flow assay device may have a single internal control region or two or more different internal control regions, where the immobilized control agents of each region may be the same or different. Each member of a control binding pair (e.g., an immobilized control agent and/or a mobile control binding agent) can be considered a "control binding pair member."

Control binding pair members may be any of the binding pair members described above, so long as they can be distinguished from the test binding pair members. Although, in general, any conventional control binding pair can be used herein, in some instances a control compound (control binding pair member) that does not exist in the sample or does not immunologically cross-react with compounds that exist in the sample is employed. Examples of suitable control binding pairs include, but are not limited to: Mouse IgG/anti-mouse IgG, chicken IgY/anti-chicken IgY, and the like. Either member of these pairs may be the immobilized control agent, with the other being the mobile control binding agent. In some embodiments, the mobile control binding agent is covalently or non-covalently linked to a reporter. In some embodiments, the mobile control binding agent includes a binding pair member.

In some embodiments, the mobile control binding agent includes a label moiety. The label moiety of the mobile control binding agent can be the same as or different than any other label moiety employed. In some embodiments, the mobile control binding agent is not linked to another molecule. In some embodiments, the mobile control binding agent is linked to a reporter (defined below).

In some embodiments, a mobile control binding agent is associated with the test lateral flow assay device prior to the addition of sample and the test lateral flow assay device can therefore be said to include a mobile control binding agent. In such cases, the mobile control binding agent is not immobilized (defined above). When associated with a test lateral flow assay device prior to the addition of sample, the mobile control binding agent is positioned upstream from the internal control region, e.g., either in the sample receiving region or a location between the sample receiving region and the internal control region. The distance between the mobile control binding agent and the internal control region may vary, ranging in some instances from 0.3 to 15 cm, such as 1 to 5 cm and including 5 to 10 cm.

In some embodiments, a reporter is associated with the test lateral flow assay device prior to the addition of sample and the test lateral flow assay device can therefore be said to include a reporter. In such cases, the reporter is not immobilized (defined above). A "reporter," which provides for signal detection, includes a specific binding member and a signal producing member that are stably associated with each other, e.g., via covalent bonding. A "specific binding member" of a reporter is a binding pair member that specifically binds a binding pair member of a competitor. Thus, a reporter can be said to specifically bind to a competitor. For example, in some embodiments, a reporter binds to a third binding pair member of a competitor.

A "signal producing system member" of a reporter is a member that provides for signal detection. As such, in some embodiments, a signal producing system member is a label moiety (e.g., a fluorescent protein, a fluorescent dye, an enzyme, a radiolabel, a metal label, a colorimetric label, and the like.). In some embodiments, a signal producing system member is a binding pair member. As mentioned above, a reporter can be linked to a mobile control binding agent. In such cases, a reporter provides for signal detection via binding to the competitor, and serves as a mobile control binding agent via binding to the immobilized control agent of the internal control region.

A reporter can be any molecule (e.g., antibody binding agents, proteins, peptides, e.g., glutathione, epitopes, tags, haptens, nucleic acids, carbohydrates, e.g., amylose, maltose, etc.) that specifically binds to the competitor. Reporters of interest can include any binding pair member, e.g., as described above. When associated with a test lateral flow assay device prior to the addition of sample, the reporter is positioned upstream from the detection region, e.g., either in the sample receiving region or a location between the sample receiving region and the detection region. The distance between the reporter and the detection region may vary, ranging in some instances from 0.3 to 15 cm, such as 1 to 5 cm and including 5 to 10 cm.

Devices of the invention can be configured to provide qualitative or quantitative results. Qualitative results include results that provide a simple "yes" or "no" determination of whether the analyte is present in the sample being assayed. Qualitative results also include results that are positive if the amount of analyte in the sample exceeds a predetermined threshold. In some embodiments where lateral flow assay device is configured to provide qualitative results, such as those where the analyte needs to be at a certain minimum concentration to be used in subsequent procedures, the assay device may be configured to have lower sensitivity than a comparable lateral flow assay device that is configured to detect the presence of the analyte at any concentration. As such, in certain instances where qualitative results in the format of an analyte simply being present in an amount that exceeds a pre-determined threshold are desired, the assay device may be configured to have a sensitivity that is not sufficient to provide detection below the threshold. If the assay device is too sensitive, then there is a risk of a false positive result where an analyte that is too low in concentration to be useful nonetheless yields a positive result. This sensitivity can be set to any minimum amount of analyte in the sample. In addition, in certain embodiments, multiple assay devices (e.g., in the form of test strips) may be supplied each with the same analyte but with different sensitivities depending on the necessary threshold for analyte utility. The desired sensitivity may be provided in a given device using any convenient protocol, e.g., by providing an appropriate amount of capture probe in the detection region, by changing the amount of first capture probe in the sample receiving region, etc.

In contrast, quantitative results provide some measurement of how much of the analyte is present in the sample being assayed. Accordingly, a quantitative result provides at least an approximation of the amount of the analyte of the interest that is present in the sample being assayed. In some embodiments, to provide for quantitative results, the detection region includes two or more distinct capture probe regions that include the same or different amounts of the same capture probe. As the amount of analyte in the sample increases, the amount of competitor that flows to the detection region increases. As such, when the amount of competitor that flows to the detection region exceeds the amount that can be captured in capture probe region #1 of the detection region, the remaining competitor will move to capture probe region #2 of the detection region. The resultant positive results from both capture probe regions of the detection region provide a quantitative measurement of the amount of analyte in the sample. By having within the detection region a series of regions, which may be a gradient of two or more capture probe regions each having differing (such as decreasing or increasing) amounts of capture probe, a quantitative measurement of the analyte in the sample may be obtained. Alternatively, quantitative measurements can be obtained by densitometry. In this case, only one capture probe region is necessary.

In some embodiments, a device is configured such that detected signal intensity increases with increasing amounts of analyte present in the sample. Thus, the intensity of the detected signal is said to be proportional to the amount of analyte present in the sample. However, in some embodiments, a device of the invention is configured such that the signal intensity has an upper limit and increasing the amount of analyte over a particular value no longer increases signal intensity.

Where desired, the component parts of the test lateral flow assay device can be present in a suitable housing. The housing can be configured to enclose the bibulous member and other assay components. The housing can be fabricated from any suitable material, where the material may be a material that is sufficiently rigid to maintain the integrity of the bibulous member and other components housed therein and also inert to the various fluids and reagents that contact the housing during use. Housing materials of interest include plastics. The housing can include a port or analogous structure configured to allow sample application to the sample application region and a window configured to allow viewing of the detection region. The housing can include markings, e.g., detection region and control region markings (e.g., "T" and "C"), etc.

An example of a lateral flow assay device which may be employed in methods of the invention is shown in FIG. 1A. In FIG. 1A, a lateral flow assay device 10 includes a housing 12 that encloses a bibulous member. Sample is applied to sample receiving region 14. Also shown is viewing window 18 which allows for visualization of the detection region 20.

Methods

Methods of the invention include providing a sample-contacted sample receiving region of a test lateral flow assay device. A "sample-contacted sample receiving region" is a sample receiving region that has been contacted by sample. In practicing methods of the invention, a sample-contacted sample receiving region is provided by applying a sample to the sample receiving region of the test lateral flow assay device. The amount of sample that is applied to the sample receiving region may vary, so long as it is sufficient to provide for the desired lateral flow and operability of the assay. The sample may be applied to the sample receiving region using any convenient protocol, e.g., via dropper, pipette, syringe and the like. In addition to providing a sample-contacted sample receiving region, the methods can further include applying a quantity of a suitable liquid, e.g., buffer, to provide for adequate fluid flow through the bibulous member. Any suitable liquid may be employed, including but not limited to buffers, cell culture media (e.g., DMEM), etc. Buffers include, but are not limited to: tris, tricine, MOPS, HEPES, PIPES, MES, PBS, TBS, and the like. Where desired, detergents may be present in the liquid, e.g., NP-40, TWEEN™ or TritonX100 detergents. Precipitating agents may also be present in the liquid, e.g., ethanol, isopropanol, etc.

In some embodiments, the sample-contacted sample receiving region is provided by combining the sample with one or more assay components (e.g., a reporter, a mobile control binding agent, a competitor, and the like) prior to applying the sample which has the assay component(s) to the sample receiving region. When the sample is combined with one or more assay components (e.g., a reporter, a mobile control binding agent, a competitor, and the like) prior to the application of the sample having the assay component(s) to the sample receiving region, the combination may be achieved using any convenient protocol. The amount of an assay component(s), when combined with the sample, may vary as desired.

In some embodiments, the sample-contacted sample receiving region is provided by applying one or more assay components (e.g., a reporter, a mobile control binding agent, a competitor, and the like) to the sample receiving region prior to applying the sample to the sample receiving region. In some embodiments, the sample-contacted sample receiving region is provided by applying the sample to the sample receiving region prior to applying one or more assay components (e.g., a reporter, a mobile control binding agent, a competitor, and the like) to the sample receiving region. As mentioned above, in some embodiments, the test lateral flow assay device includes one or more assay components (e.g., a reporter, a mobile control binding agent, a competitor, and the like). In such cases, the sample-contacted sample receiving region is provided by applying the sample to the sample receiving region.

Following sample application, the sample is allowed to laterally flow through the bibulous member and detection region, and the detection region is then read to determine whether the analyte is present in the sample. The detection region may be read after a predetermined period of time following sample application, where this period of time may range from 10 sec to 1 hour, such as 30 sec to 30 min, e.g., 30 sec to 10 min, including 30 sec to 1 min The detection region is read using a protocol that depends on the nature of the detectable product of the signal. Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, metal labels can be detected by simply visualizing the colored label or can be detected using laboratory equipment capable of detecting metal, and colorimetric labels are detected by simply visualizing the colored label. Accordingly, in those instances where the detectable product of the signal producing system is a colored label, the method may include visually inspecting the detection region, e.g., through the viewing window of a housing of the device. As such, a subsequent step in methods of the invention includes reading a detection region of the test lateral flow assay device to determine whether the analyte is present in the sample.

In some embodiments, the method is a method of determining whether an analyte is present in the sample in an amount that meets or exceeds a predetermined threshold. As such, when the amount of analyte of interest in the sample surpasses a particular threshold (also referred to as a "predetermined threshold"), the signal in the detection region (resulting from the binding of competitor to capture probe in the detection region) is detectable. The threshold or predetermined threshold is determined by multiple differentially weighted factors (e.g., the number of capture probes in the sample receiving region that bind to the analyte, the binding affinity of the capture probe for the analyte, the binding affinity of the capture probe for the competitor, the amount of analyte present, the amount of competitor present, the ratio of analyte present to competitor present, viscosity, pH, temperature, and the like).

FIGS. 1B and 1C provide illustrations of the device shown in FIG. 1A in which a negative result has been obtained (FIG. 1B) and a positive result has been obtained (FIG. 1C). In FIG. 1B, the only stripe visible and therefore detected in the detection region 20 of the device 10 is the internal control stripe 22. The presence of the control stripe 22 and absence of any test stripe in region "T" 24 indicates that no analyte was present in the assayed sample, but the assay was working correctly as demonstrated by the presence of the internal control stripe 22. In FIG. 1C, both the internal control stripe 22 and the test strip 24 are visible and therefore detected in the detection 20 region of device 10. The presence of the control stripe 22 and the test stripe 24 in region "T" indicates that analyte was present in the assayed sample and the assay was working correctly as demonstrated by the presence of the internal control stripe 22.

In some instances, the methods of the invention are employed as one step in a multi-step research protocol, where the protocol at least includes a further step either before or after the step of analyte detection. Therefore, aspects of the invention include a research protocol that includes a first step, an analyte detection step and then a subsequent step. For example, in some instances methods of the invention include a step of preparing the sample, a step of testing the sample for the analyte of interest, and then a step of further using the sample in a research procedure, e.g., a further method performed in a laboratory.

In some embodiments, the sample (containing or not containing the analyte of interest) is produced prior to the detection step. In some instances, the analyte of interest is a "tagged analyte", which is an analyte that is covalently or non-covalently linked to a binding pair member (e.g., a histidine tag, a FLAG tag, a c-MYC tag, a hemagglutinin (HA) tag, a glutathione-S-transferase (GST) tag, a maltose-binding protein (MBP) tag, a calmodulin-binding peptide (CBP) tag, a chitin-binding domain (CBD) tag, an Avitag, a S-tag, a tandem affinity purification (TAP) tag, a VSV-G tag, a Strep-tag, an HSV tag, a V5 tag, biotin, DNP, fluorescein, and the like). In some cases, a sample having a tagged analyte is produced prior to the detection step. To accomplish this, an epitope-tagged protein (i.e., "fusion protein", a protein that includes a tag) can be produced in any one of a variety of systems, such as a bacterial expression system (e.g., $E.\ coli$), fungal expression system (e.g., $S.\ cerevisiae$), viral expression system, and the like. Samples can include protein preparations (e.g., obtained from lysed bacterial cells). Such compositions can be generated from cell cultures or tissues by preparing a cell extract (e.g., lysing the cells by suspending in lysis buffer and vortexing, inverting, or homogenizing the suspension; optionally treating the suspension with nuclease; and optionally exchanging the extracted constituents into an appropriate buffer for the methods described herein, e.g. via dialysis) from cells expressing an analyte of interest (e.g., tagged recombinant protein, fusion protein, tagged protein, and the like). The composition can include contaminants, e.g. bacterial endotoxin and the like. An analyte of interest may be purified using methods such as chromatography (e.g. affinity, ion exchange, size-exclusion, and the like), selective precipitation, filtration, and the like. As such, the analyte of interest can be purified or non-purified. The sample in such cases is a protein preparation (purified or non-purified) that includes a fusion protein (tagged analyte of interest).

A detection step may then be performed by applying a fraction of the sample to the sample receiving region of a lateral flow assay which has a capture probe (e.g. tag-specific monoclonal or polyclonal antibody and the like), optionally a competitor that includes a label moiety, and/or optionally a reporter that includes a label moiety. If sufficient quantities of the epitope-tagged protein are applied to such a lateral flow assay, then a visible signal will indicate the presence of the epitope tag. In some embodiments, the methods include determining whether a tagged analyte is present in the sample in an amount that meets or exceeds a predetermined threshold. In such cases, the determination of whether an analyte is present in an amount that meets or exceeds a predetermined threshold can be used to further determine whether or not to proceed to the next step in a research protocol. A quantitative estimate of the amount of expressed protein present in the sample can be obtained using strips having multiple capture probe regions, or by densitometry, or by titrating the sample against the competitor.

In some embodiments, the analyte to be detected is a nucleic acid. Samples can be nucleic acid (e.g., DNA and RNA) preparations (e.g., obtained from lysed bacterial cells, in vitro reactions, and the like). Samples containing a nucleic acid analyte can be generated from bacterial cultures by harvesting bacteria, e.g. by centrifugation; resuspending and lysing the bacteria, e.g. by vortexing; precipitating nucleic acid, e.g., DNA, from the lysate, e.g. by adding ethanol; and collecting the precipitated nucleic acid from the lysate, e.g. by column purification or centrifugation and resuspension. A nucleic acid preparation obtained by such means can include DNA and an elution or resuspension buffer (e.g. tris, tricine, MOPS, HEPES, PIPES, MES, and the like) and salts (e.g. sodium chloride, sodium acetate, sodium citrate, sodium phosphate, magnesium chloride, magnesium acetate, potassium chloride, potassium phosphate, potassium acetate, calcium chloride, calcium acetate, calcium phosphate, ammonium chloride, ammonium acetate, and the like). In addition, the composition can further include contaminants, e.g. bacterial endotoxin and the like.

A nucleic acid analyte can also be generated from an in vitro reaction (e.g., a PCR reaction, an in vitro mRNA transcription reaction, and the like). As is known in the art, in vitro mRNA transcription reaction mixtures can be added to an in vitro translation system to direct synthesis of a protein encoded by the mRNA. In vitro mRNA transcription reaction mixtures can be generated by combining a DNA template with RNA polymerase, nucleotide triphosphates, and an appropriate buffer and incubating the resultant at an appropriate temperature for various durations. Tags (e.g., DNP-uridine triphosphate (UTP), fluorescein-UTP, biotin-UTP, DIG-UTP, and the like) can be added to the reaction mixture to be incorporated into the final product. A successful, completed reaction mixture can include synthesized mRNA, RNA polymerase, and various other components, such as but not limited to buffers (e.g. tris, tricine, MOPS, HEPES, PIPES, MES, and the like), salts (e.g. sodium chloride, sodium acetate, sodium citrate, sodium phosphate, magnesium chloride, magnesium acetate, potassium chloride, potassium phosphate, potassium acetate, calcium chloride, calcium acetate, calcium phosphate, ammonium chloride, ammonium acetate, and the like), and other small molecules (e.g. nucleotides, reducing agents such as dithiothreitol, and the like).

The nucleic acid analyte to be detected can be a tagged nucleic acid. For example, it may be desirable to know whether a nucleic acid analyte synthesized by an in vitro mRNA synthesis reaction is present in a sample in an amount greater than a predetermined threshold prior to proceeding to a next step in a protocol (e.g., in vitro translation reaction, in situ hybridization experiment, and the like). As one non-limiting example, a nucleic acid analyte may have been synthesized in the presence of (DNP-UTP, fluorescein-UTP, DIG-UTP, or biotin-UTP). In such a case, a first capture probe can be an anti-DNP, anti-fluorescein, or anti-DIG antibody; or avidin, streptavidin, or neutravidin and the methods can include determining whether the tagged nucleic acid analyte is present in the sample in an amount that meets or exceeds a predetermined threshold. Where desired, a quantitative estimate of the amount of synthesized nucleic acid analyte present in the sample can be obtained using strips having multiple capture probe regions, or by densitometry, as described above.

In some embodiments, the analyte to be detected may be a reporter protein, e.g. luciferase, fluorescent proteins (such as green fluorescent protein and the like), β-galactosidase, β-glucuronidase, and the like. For example, an expression construct containing a reporter gene (such as those just described) driven by an experimental transcription factor can be generated and cells having the construct can be cultured under various stress conditions (such as starvation, heat or cold treatment, nutrient or salt abundance or deprivation, and the like). A cellular supernatant or extract can then be generated. The analyte detection step can be used to determine the presence, absence, or quantity of the expressed reporter protein, thus allowing the researcher to determine whether the transcription factor was active under the stress conditions, whether to continue with subsequent steps of the protocol, etc. Alternatively, the method may be employed to confirm transfection. For example, a secreted protein may be assayed to confirm successful transfection.—e.g. by detecting the presence of the secreted protein in the supernatant of successfully transfected cells. Confirmation of transfection may then be used as indication that the cells are suitable for use in further experiments. Where desired, a quantitative estimate of the amount of expressed protein present in the sample can be obtained using strips having multiple capture probe regions, or by densitometry, as described above.

In some embodiments, the analyte to be detected is a viral vector (e.g., viral particle) that is present in a viral vector packaging supernatant. In this case, the analyte detection step may be preceded by generation of a viral vector supernatant that is generated for use in viral expression protocols, such as those used in lentiviral expression systems, baculoviral expression systems, adenoviral expression systems, retroviral expression systems, and the like. Viral vector packaging supernatants can be generated in a research laboratory by transfecting a packaging cell line, e.g. HEK 293 cells, Sf21 cells, NIH 3T3 cells, and the like, with a competent vector such as, but not limited to: pLVX and its derivatives, pBac-PAK8 and its derivatives, pShuttle2 and its derivatives, pRetro-Lib, plasmids derived from MMLV (such as pLXRN, pLNHX, pLNCX, pLNCX2, etc.), and the like. Following transfection, the cells are grown in a suitable growth medium to achieve a desired viral titre. Next, the cell culture can be subjected to centrifuging and/or filtering to separate the supernatant from the cells. The resultant supernatant can include mature virus particles as well as components that are derived from the growth medium, including components found in growth medium such as, but not limited to, Dulbecco's Modified Eagle's Medium (DMEM), glucose, L-glutamine, sodium bicarbonate, fetal bovine serum, sodium pyruvate, and the like.

At this stage, an analyte detection step may be used to ensure that virus is present in the harvested supernatant prior to subsequent transduction steps. If the supernatant contains a quantity of mature virus at a concentration sufficient to support transduction of target cells, e.g. $>5 \times 10^5$ infectious units per milliliter (IFU/mL), then the detection capture probe will capture sufficient quantities of competitor to produce a visible signal and indicate the presence of the virus. The supernatant can then be used to reliably transduce target cells. Lateral flow assays can be employed to test for the presence of various viruses in supernatant, such as baculovirus, retroviruses, and the like. A quantitative estimate of the amount of virus present in the sample can be obtained using strips having multiple capture probe regions, or by densitometry, as described above.

In some embodiments, the analyte to be detected may be a laboratory contaminant, e.g. mycoplasma and the like. In this case, the analyte detection step may be employed at any time during a multi-step research protocol to test for the presence of a contaminating agent. The detection step's indication of the absence or presence of such contaminating agents will dictate whether any subsequent experiment sensitive to such agents, e.g. tissue culture, may proceed or must be aborted. A quantitative estimate of the amount of expressed protein present in the sample can be obtained using strips having multiple capture probe regions, or by densitometry, as described above.

In some embodiments, the analyte to be detected may be a sample contaminant, such as bacterial endotoxin, culture contaminants such as mycoplasma, and the like. In this case, a researcher may prepare a sample of DNA, protein, or another molecule from a bacterial (or other appropriate, e.g., cell culture) source and wish to check for contamination prior to using the preparation in subsequent experiments. The researcher may use an analyte detection step to ensure that the preparation is free of contaminant, e.g., endotoxin, mycoplasma, etc., prior to further experiments involving the composition of interest.

In some embodiments, samples can be purified prior to being assayed using a test lateral flow assay device. A purified sample can be a chromatography eluent (e.g., an eluant from a fast protein liquid chromatography (FPLC) column). Such an eluant can be obtained by applying a sample (e.g., produced from lysates from bacteria, yeast, insect or mammalian cells) using any suitable method known in the art) to a chromatography column, such as a size-exclusion column, affinity column, ion exchange column, metal ion affinity column, hydrophobic interaction column, and the like; moving the protein sample through the column (e.g., using an FPLC pump or allowing the sample to flow via gravity); and collecting the column eluant in multiple fractions. Any given fraction can include numerous analytes of interest, analytes not of interest, column buffer, and sample buffer (e.g. tris, tricine, MOPS, HEPES, PIPES, MES, and the like), salts (e.g. sodium chloride, sodium acetate, sodium citrate, sodium phosphate, magnesium chloride, magnesium acetate, potassium chloride, potassium phosphate, potassium acetate, calcium chloride, calcium acetate, calcium phosphate, ammonium chloride, ammonium acetate, and the like), and other small molecules (e.g. amino acids, nucleotides, sugars, reducing agents such as dithiothreitol and β-mercaptoethanol, and the like).

The methods of the invention are methods of using a lateral flow assay device to determine whether an analyte is present in a sample and the methods are based on a principle of competition. Accordingly, a competitor competes with an analyte for binding to the first capture probe. Thus, the competitor (via the first binding pair member) competes with the analyte of interest for binding to the first capture probe and the competitor (e.g., via the first binding pair member or via the second binding pair member) specifically binds to the detection capture probe. In some cases, the analyte and competitor include an identical binding pair member (e.g., an MBP tag, a GST tag, a histidine tag, and the like) and the first capture probe specifically binds to the binding pair member. For example, in some embodiments, the first capture probe is an antibody that specifically binds to a histidine tag and a histidine tag of the analyte is identical to a histidine tag of the competitor.

In some embodiments, the analyte includes a binding pair member that is different than the binding pair member of the competitor, but both binding pair members specifically bind to the first capture probe (the first capture probe can therefore be considered to include a binding pair member that can form a binding pair with either the binding pair member of the analyte or the binding pair member of the competitor). For example, in some embodiments, the first capture probe is an antibody that specifically binds to a histidine tag, and a histidine tag of the analyte differs from a histidine tag of the competitor, but the first capture probe can specifically bind to either histidine tag. In some embodiments, the first capture probe is an immobilized metal ion (e.g., $Ni^{+2}$, $Co^{+2}$, $Fe^{+3}$, $Al^{+3}$, $Zn^{+2}$, $Cu^{+2}$, and the like) that specifically binds to a metal ion affinity peptide, and a histidine tag of the analyte differs from a histidine tag of the competitor, but both histidine tags specifically bind the first capture probe (the immobilized metal ion). In some embodiments, the first capture probe is an immobilized metal ion (e.g., $Ni^{+2}$, $Co^{+2}$, $Fe^{+3}$, $Al^{+3}$, $Zn^{+2}$, $Cu^{+2}$, and the like) that specifically binds to a metal ion affinity peptide and a metal ion affinity peptide of the analyte differs from a metal ion affinity peptide of the competitor, but both metal ion affinity peptides specifically bind to the first capture probe (immobilized metal ion).

Figure 3:
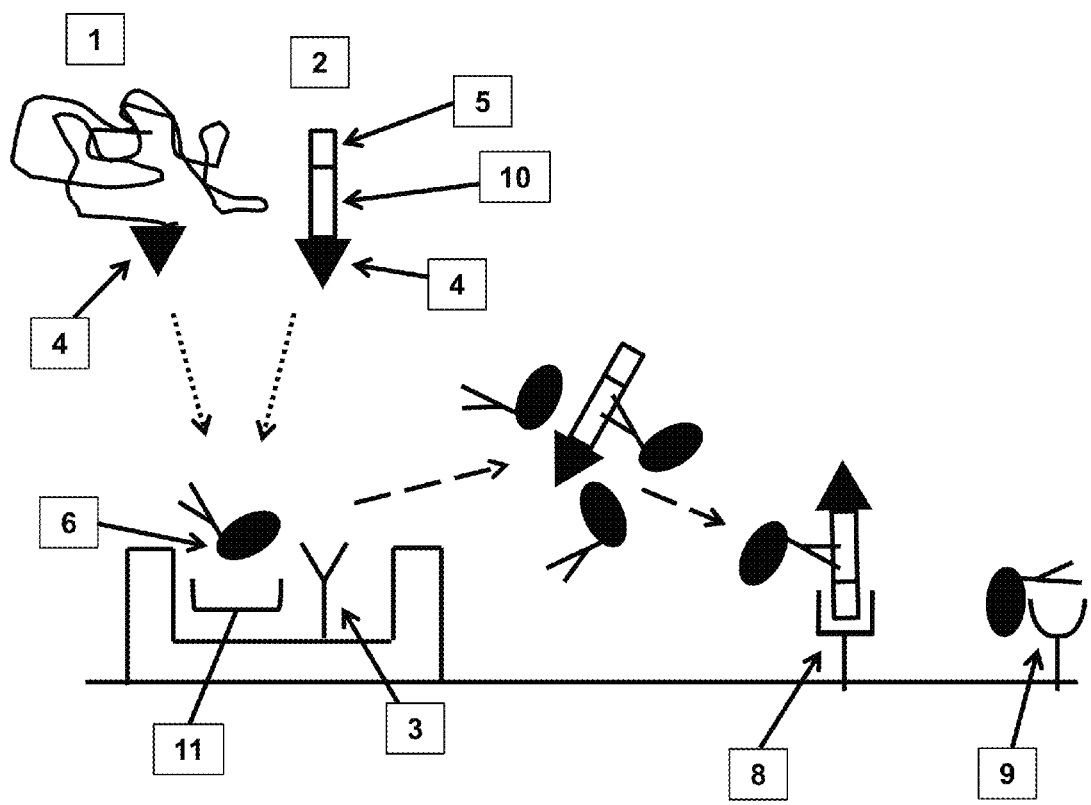
FIG. 3 is a schematic of one embodiment of a lateral flow assay method. The embodiment depicted employs a reporter 11 that is linked to a mobile control binding agent and includes a label moiety 6. The analyte 1 and competitor 2 contact the reporter 11 prior to contacting a first capture probe 3 in the sample receiving region 20.

In embodiments that employ a reporter, the sample and the competitor can contact a reporter prior to or after contacting a first capture probe. In some embodiments, the competitor and the sample contact the reporter prior to contacting the first capture probe (FIG. 3). In some embodiments, the competitor and the sample contact the first capture probe prior to contacting the reporter (FIG. 4).

In some embodiments, the methods include applying a control sample to a sample receiving region of a control lateral flow assay device and reading a detection region of the control lateral flow assay device to obtain a result. In these embodiments, the control lateral flow assay device is identical (e.g., a second lateral flow device from the same production lot as the test lateral flow device) to the test lateral flow assay device. The control sample is a fluid sample that includes a known amount of the analyte of interest. As such, these embodiments employ running a complete control assay using a lateral flow assay device that is the same as the test lateral flow assay device.

Figure 2:
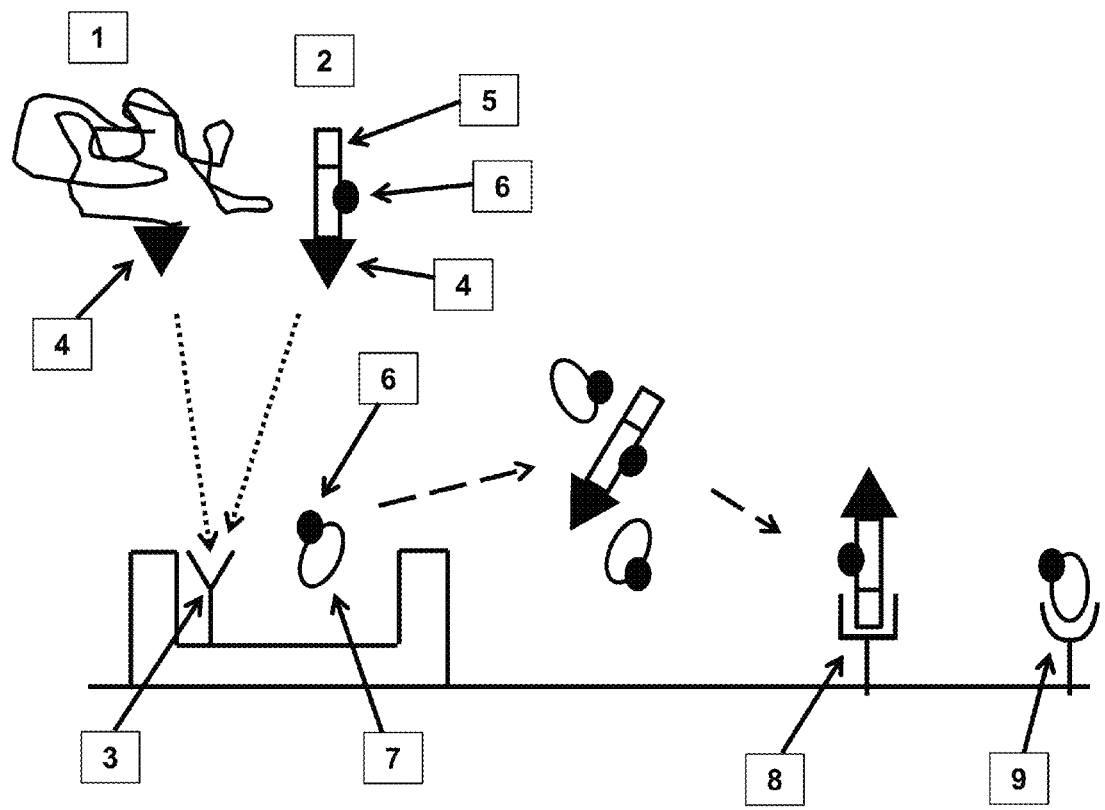
FIG. 2 is a schematic of one embodiment of a lateral flow assay method. The embodiment depicted employs a mobile control binding agent 7 and a labeled competitor 2.
Figure 4:
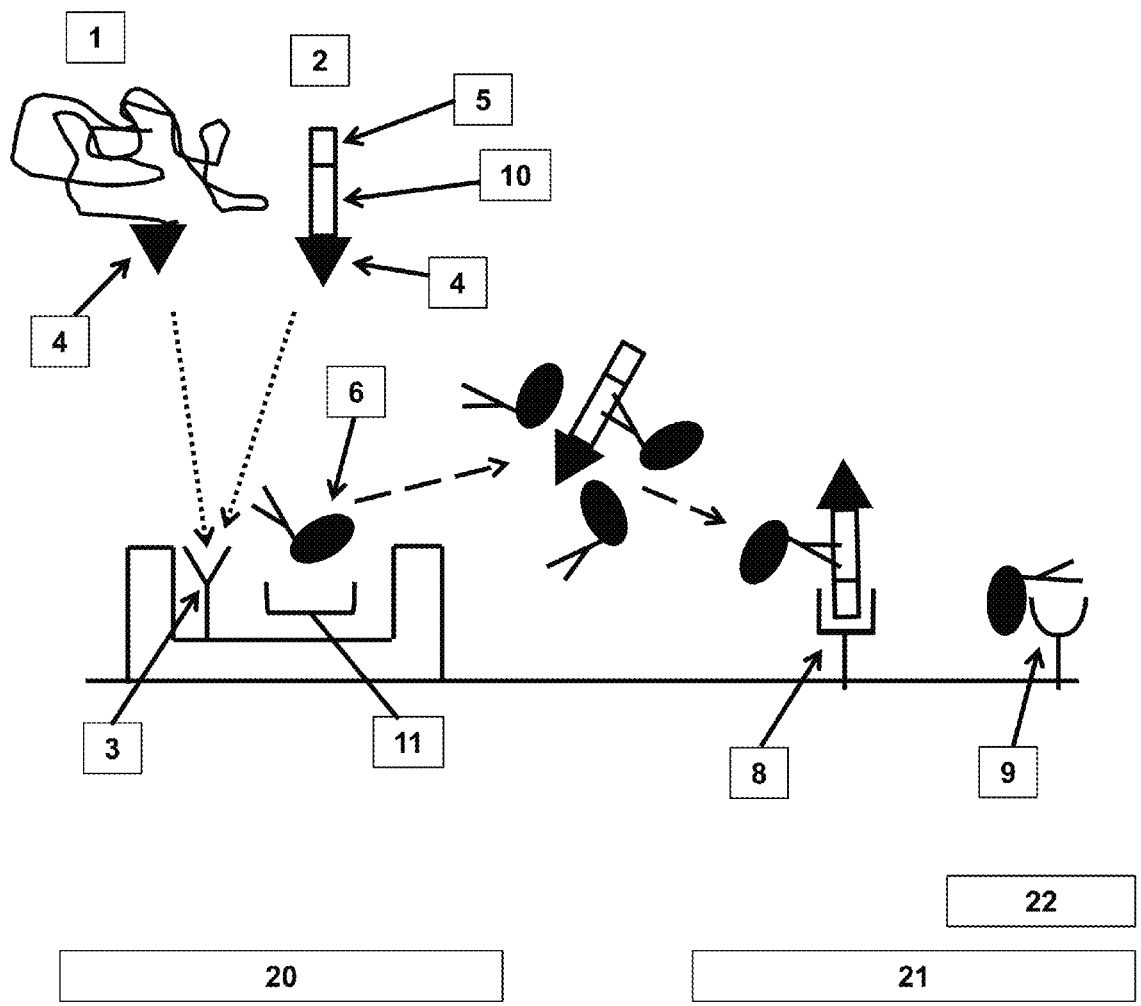
FIG. 4 is a schematic of one embodiment of a lateral flow assay method. The embodiment depicted is identical to that of FIG. 3 with the exception that the analyte 1 and competitor 2 contact the first capture probe 3 prior to contacting the reporter 11.

FIGS. 2-4 provide schematics of three different embodiments of the above described methods. The embodiment depicted in FIG. 2 employs a mobile control binding agent 7 and a labeled competitor 2. Once sample is added, an analyte 1 and a competitor 2, each sharing the same first binding pair member 4, compete for binding to a first capture probe 3 of the sample receiving region 20. The competitor 2 further includes a second binding pair member 5 and a label moiety 6. When the amount of analyte 1 is high enough, competitor 2 is outcompeted for binding to the first capture probe 3 and competitor 2 flows to the detection region 21, where competitor 2 binds to a detection capture probe 8 via the second binding pair member 5 of the competitor 2. Signal is detected in the detection region 21 via the label moiety 6 of the competitor 2. In addition, a mobile control binding agent 7, which includes the same label moiety 6 as that of the competitor 2, is present in the sample-contacted sample receiving region 20 and flows to the internal control region 22 where it binds to an immobilized control agent 9. Signal is detected in the internal control region 22 via the label moiety 6 of the mobile control binding agent 7.

The embodiment depicted in FIG. 3 employs a reporter 11 that is linked to a mobile control binding agent and includes a label moiety 6. The analyte 1 and competitor 2 contact the reporter 11 prior to contacting a first capture probe 3 in the sample receiving region 20. The analyte 1 and competitor 2 each include the same first binding pair member 4 and the competitor 2 further includes a second binding pair member 5 and a third binding pair member 10. The reporter 11 specifically binds to the third binding pair member 10 of the competitor 2. The analyte 1 and competitor 2 compete for binding to the first capture probe 3. When the amount of analyte 1 is high enough, competitor 2 is outcompeted for binding to the first capture probe 3 and competitor 2 flows to the detection region 21, where competitor 2 binds to a detection capture probe 8 via the second binding pair member 5 of the competitor 2. Signal is detected in the detection region 21 via the label moiety 6 of the reporter 11 that is bound to the competitor 2. Because the reporter 11 is linked to a mobile control binding agent, the reporter serves as an internal control and the reporter 11 binds to an immobilized control agent 9 in the internal control region 22.

The embodiment depicted in FIG. 4 is identical to the embodiment depicted in FIG. 3 with the exception that the analyte 1 and competitor 2 contact the first capture probe 3 prior to contacting the reporter 11.

Utility

The methods, devices, and kits of the invention find use in a variety of different applications and can be used to determine whether an analyte is present in a multitude of different sample types from a multitude of possible sources. Depending on the application and the desired output of the methods described herein, an analyte may be detected in a qualitative manner ("present" vs "absent"; "yes, above a predetermined threshold" vs "no, not above a predetermined threshold"; etc.) or a quantitative manner, as described above. Also as described above, many different types of analytes can be analytes of interest, including but not limited to: a tagged analyte, a nucleic acid analyte, a reporter protein, a viral vector, a lab contaminant, a sample contaminant, and the like. Further, samples can be from in vitro or in vivo sources, and samples can be non-diagnostic or diagnostic samples.

In practicing methods of the invention, the samples can be obtained from in vitro sources (e.g., extract from a laboratory grown cell culture) or from in vivo sources (e.g., a mammalian subject, a human subject, a research animal expressing a tagged analyte of interest, etc.). In some embodiments, the sample is obtained from an in vitro source. In vitro sources include, but are not limited to, prokaryotic (e.g., bacterial) cell cultures, eukaryotic (e.g., mammalian, fungal) cell cultures (e.g., cultures of established cell lines, cultures of known or purchased cell lines, cultures of immortalized cell lines, cultures of primary cells, cultures of laboratory yeast, etc.), tissue cultures, column chromatography eluants, cell lysates/extracts (e.g., protein-containing lysates/extracts, nucleic acid-containing lysates/extracts, etc.), viral packaging supernatants, and the like. In some embodiments, the sample is obtained from an in vivo source. In vivo sources include living multi-cellular organisms and can yield non-diagnostic or diagnostic samples.

In some embodiments, the analyte is a non-diagnostic analyte. A "non-diagnostic analyte" is an analyte from a sample that has not been obtained from or derived from a living multi-cellular organism, e.g., mammal, in order to make a diagnosis. In other words, the sample has not been obtained to determine the presence of one or more disease analytes in order to diagnose a disease or condition. Accordingly, in some instances, methods of the invention are non-diagnostic methods. "Non-diagnostic methods" are methods that do not diagnose a disease (e.g., sickness, diabetes, etc.) or condition (e.g., pregnancy) in a living organism, such as a mammal (e.g., a human). As such, non-diagnostic methods are not methods that are employed to determine the presence of one or more disease analytes in order to diagnose a disease or condition.

In certain embodiments, the methods are methods of determining whether a non-diagnostic analyte is present in a non-diagnostic sample. As such, the methods are methods of evaluating a sample in which the analyte of interest may or may not be present. In some cases, it is unknown whether the analyte is present in the sample prior to performing the assay. In other instances, prior to performing the assay, it is unknown whether the analyte is present in the sample in an amount that is greater than (exceeds) a predetermined threshold amount. In such cases, the methods are methods of evaluating a sample in which the analyte of interest may or may not be present in an amount that is greater than (exceeds) a predetermined threshold.

Aspects of the non-diagnostic methods include determining whether a non-diagnostic analyte is present in a non-diagnostic sample. Non-diagnostic samples can be obtained from in vitro sources, e.g., prokaryotic cell cultures (e.g., bacterial cell cultures); eukaryotic cell cultures (e.g., mammalian cell cultures); tissue cultures; non-diagnostic animal tissue samples or body fluids (i.e., such samples when not being used for diagnosis); column chromatography devices; and the like, or from in vivo sources (e.g., a sample obtained from living multicellular organism).

In some instances, non-diagnostic samples that are tested using lateral flow methods are samples generated in a research laboratory, for example, samples that are obtained from research experiments, including biotechnology research experiments (such as in vitro experiments that may or may not employ living cells, recombinant vectors, synthesized proteins, etc). Examples of research experiment samples include, but are not limited to: cell and tissue cultures (and derivatives thereof, such as supernatants, lysates, and the like.); non-diagnostic animal tissue samples and body fluids; non-cellular samples (e.g., column eluants; acellular biomolecules such as proteins, lipids, carbohydrates, nucleic acids, etc; in vitro synthesis reaction mixtures; nucleic acid amplification reaction mixtures; in vitro biochemical or enzymatic reactions or assay solutions; or products of other in vitro and in vivo reactions; viral vector packaging supernatants; etc). As used herein, research experiment samples exclude environmental samples, e.g., samples that are obtained from the environment in order to determine some quality or aspect of the environment, such as presence of one or more toxins, peptides, proteins, nucleic acids, or small molecules, and the like.

In some instances, non-diagnostic samples differ from a diagnostic sample by including components not found in diagnostic samples and/or lacking components found in diagnostic samples. In some instances, the contents of a non-diagnostic sample are readily determined because the non-diagnostic sample has been prepared from known starting materials in a research laboratory under defined and controlled conditions and protocols. In contrast, a physiological sample obtained for diagnostic purposes is inherently of unknown content, since individuals vary in terms genetic makeup and exposure to environment conditions.

In some embodiments, the analyte is a diagnostic analyte. A "diagnostic analyte" is an analyte from a sample that has been obtained from or derived from a living multi-cellular organism, e.g., mammal, in order to make a diagnosis. In other words, the sample has been obtained to determine the presence of one or more disease analytes in order to diagnose a disease or condition. Accordingly, the methods are diagnostic methods. As the methods are "diagnostic methods," they are methods that diagnose (i.e., determine the presence or absence of) a disease (e.g., sickness, diabetes, etc.) or condition (e.g., pregnancy) in a living organism, such as a mammal (e.g., a human). As such, certain embodiments of the present disclosure are methods that are employed to determine whether a living subject has a given disease or condition (e.g., diabetes). "Diagnostic methods" also include methods that determine the severity or state of a given disease or condition.

In certain embodiments, the methods are methods of determining whether an analyte is present in a diagnostic sample. As such, the methods are methods of evaluating a sample in which the analyte of interest may or may not be present. In some cases, it is unknown whether the analyte is present in the sample prior to performing the assay. In other instances, prior to performing the assay, it is unknown whether the analyte is present in the sample in an amount that is greater than (exceeds) a predetermined threshold amount. In such cases, the methods are methods of evaluating a sample in which the analyte of interest may or may not be present in an amount that is greater than (exceeds) a predetermined threshold.

Diagnostic samples include those obtained from in vivo sources (e.g., a mammalian subject, a human subject, and the like.) and can include samples obtained from tissues or cells of a subject (e.g., biopsies, tissue samples, whole blood, fractionated blood, hair, skin, and the like). In some cases, cells, fluids, or tissues derived from a subject are cultured, stored, or manipulated prior to evaluation and such a sample can be considered a diagnostic sample if the results are used to determine the presence, absence, state, or severity of a disease (e.g., sickness, diabetes, etc.) or condition (e.g., pregnancy) in a living organism.

In some instances, a diagnostic sample is a tissue sample (e.g., whole blood, fractionated blood, plasma, serum, saliva, and the like) or is obtained from a tissue sample (e.g., whole blood, fractionated blood, plasma, serum, saliva, skin, hair, and the like). An example of a diagnostic sample includes, but is not limited to cell and tissue cultures derived from a subject (and derivatives thereof, such as supernatants, lysates, and the like); tissue samples and body fluids; non-cellular samples (e.g., column eluants; acellular biomolecules such as proteins, lipids, carbohydrates, nucleic acids; synthesis reaction mixtures; nucleic acid amplification reaction mixtures; in vitro biochemical or enzymatic reactions or assay solutions; or products of other in vitro and in vivo reactions, etc.); etc.

The subject methods can be employed with samples from a variety of different types of subjects. In some embodiments, a sample is from a subject within the class mammalia, including e.g., the orders carnivore (e.g., dogs and cats), rodentia (e.g., mice, guinea pigs, and rats), lagomorpha (e.g. rabbits) and primates (e.g., humans, chimpanzees, and monkeys), and the like. In certain embodiments, the animals or hosts, i.e., subjects are humans.

Kits

Aspects of the invention further include kits, where kits include one or more test lateral flow assay devices for practicing methods of the invention. Test lateral flow assay devices of the kits include an immobilized first capture probe (sample receiving region) and an immobilized detection capture probe (detection region). In some embodiments, devices of the kits further include one or more assay components (e.g. a competitor, a reporter, a mobile control binding agent, and the like). Any assay component can be included as part of a test lateral flow assay device or can be included in a kit separate from the test lateral flow assay device. As such, in addition to a test lateral flow assay device, kits can include one or more assay components (e.g., a competitor, a reporter, a mobile control binding agent, a buffer, a reagent for dilution, a reagent for reconstitution, a sample applicator, and the like). The various assay components of the kits may be present in separate containers, or some or all of them may be precombined into a reagent mixture.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The following examples are offered by way of illustration and not by way of limitation.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second (s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Materials and Methods
Materials: Preparation of Beads (Reporter)

500 µl of gold particles were added to a first tube ("tube 1") in addition to 900 µl 20 mM MES (2-(N-Morpholino)ethanesulfonic acid, or 4-Morpholineethanesulfonic acid), pH 6.0. Tube 1 was centrifuged at 600×g for about 20 min to pellet the particles. Particles were washed twice with 900 µl 20 mM MES, pH 6.0 and centrifuged between each wash for 20 min at 600×g. Separately, 5 mg Sulfo-NHS was dissolved in 200 µl 20 mM MES, pH 6.0 (25 µg/µl). Also separately, 5 mg EDC-HCl (N-(3-Dimethylaminopropyl)-N'-ethylcarbodiimide hydrochloride), was dissolved in 200 µl 20 mM MES, pH 6.0 (25 µg/µl). 1 mL 20 mM MES, pH 6.0, 44 µl of the 25 µg/µl NHS solution (see above), and 2.16 µl of the 25 µg/µl EDC-HCl solution (see above), were added to a new a second tube ("tube 2"). The contents of tube 2 were added to the particles in tube 1 and incubated for about 15 min at RT, on rotator. Tube 1 was centrifuged for 20 minutes at 4° C. at 600×g. Reaction solution was removed and remaining particles were washed three times with 900 µl 20 mM MES, pH 6.0. For each wash, Tube 1 was centrifuged for 20 min at 600×g at 4° C. 300 µl 20 mM MES buffer, pH 6, 0.5% Tween 20 was added to particles and the particles were sonicated until the solution turned dark brown/purple. 1 mg Rockland anti-GST antibody (supplied in solution, used entire contents of tubes) was added to the particles and the mixture was incubated overnight on a rotator at 4° C. The reaction was then centrifuged for 20 minutes at 4° C. at 600×g. The particles were washed three times with 1 mL 20 mM Tris pH 7.4, 0.25% tween 20.

At this point, if the particles were to be used in a Western style of analysis, the particles were resuspended in 500 µl 20 mM Tris pH 7.4, 0.25% Tween 20, and stored at 4° C. If instead the particles were to be used for test strip assembly, the particles were resuspended in 750 µl 30% sucrose solution. 10 µl of the particle-sucrose solution was then added to a conjugate pad material that had been pre-cut into squares about 1 cm² in size. The squares were then covered and allowed to dry.

Materials: Preparation of Test Strips

Figure 5:
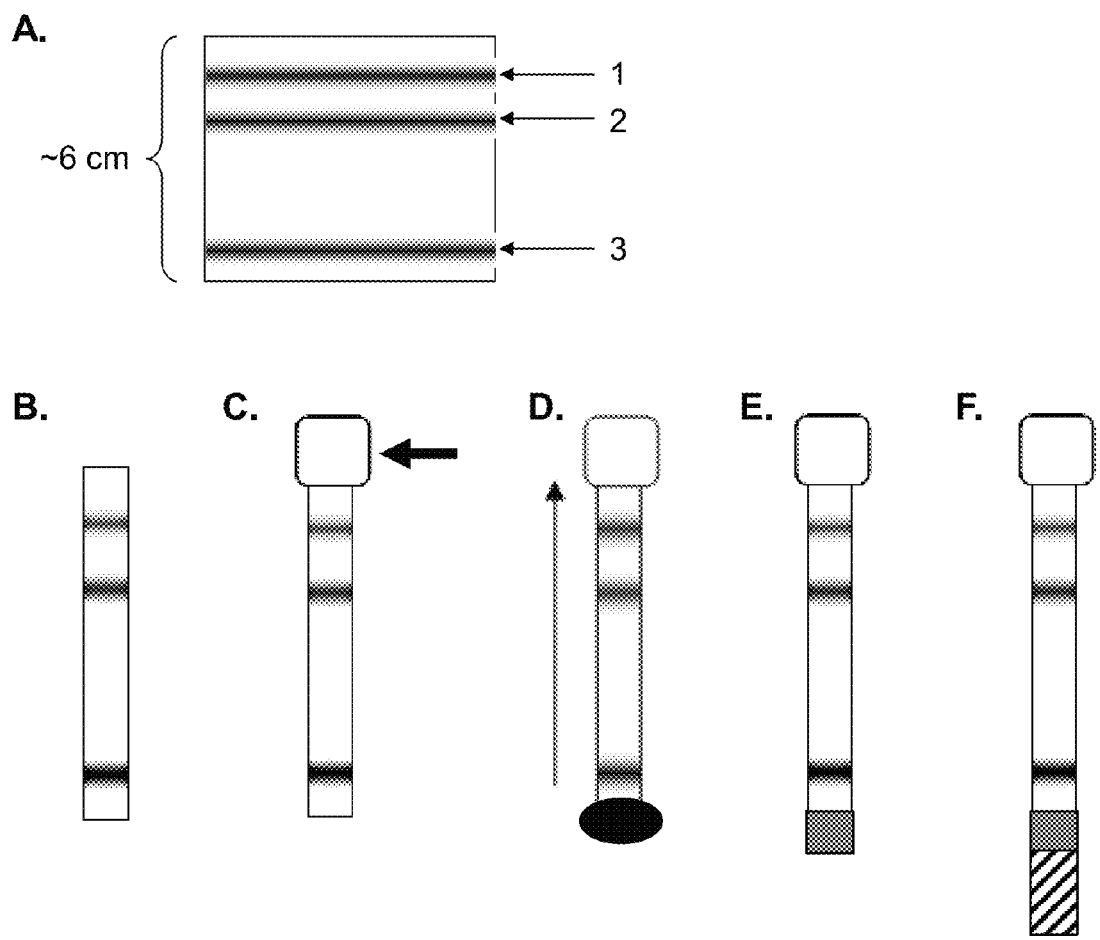
FIG. 5 Illustrates embodiments of the subject methods. 5A Depicts an exemplary sprayed membrane (test strip). From top to bottom: a positive control line 1 (an immobilized control agent, e.g., secondary antibody, GST protein line, etc.); a detection line 2 (a second capture probe); and a first capture probe 3. 5B Depicts an example of a test strip cut to about 0.8 cm wide and about 6 cm long. 5C Depicts a cellulose absorbent pad (arrow) placed on top of (i.e., at the end of) the test strip. 5D Depicts placement of sample (black oval) onto the test strip, below (i.e., prior to) the first capture probe line. The arrow indicates direction of sample flow. 5E Depicts a labeled conjugate pad (gray box), having a reporter, placed below (i.e., prior to) the first capture probe line. 5F Depicts placement of a sample pad (striped box) (i.e., unlabeled pad, or untreated pad) below (i.e., prior to) and slightly overlapping with a labeled conjugate pad of 5E.

A membrane was sprayed such that the top line included the immobilized control agent (positive control line, e.g., secondary antibody, GST protein, etc.), the next line down included the second capture probe (detection line, e.g., GST antibody), and the bottom line included the first capture probe (e.g., anti-His antibody) (FIG. 5A). Sheets were then covered and the antibody lines were allowed to dry at room temperature (approximately 1 hour). The membrane was blocked with 3% Bovine Serum Albumin (BSA) in PBS (phosphate buffered saline) for 30 minutes with agitation. The membrane was rinsed one time with PBS, rinsed a second time with 0.5×PBS, rinsed a third time with 0.1×PBS, and rinsed a fourth time with ddH$_2$O. Strips were covered and allowed to dry at room temperature (up to 30° C.) (approximately 2-3 hours). Strips were then cut to about 0.8 cm wide and about 6 cm long (FIG. 5B). Unused strips were covered in a dry location. A cellulose absorbent pad was placed on top of each strip (FIG. 5C).

Assay Protocol: Western Style Analysis

For Western style analysis, 50 µl of sample was mixed with 50 µl of dilution buffer (2×PBS with 2% ethanol, 2 ng/µl GST-His and 1% Tween 20). 75 µl of the mixture was placed onto the test strip below the first capture probe (FIG. 5D). The sample was allowed to wick across the test strip and into the absorbent pad (approximately 4 minutes). 150 µl of wash buffer (PBS with 1% ethanol and 0.5% Tween 20) was placed onto the same location the sample was placed and the wash buffer was allowed to wick into the absorbent pad (approximately 4 minutes). 20 µl of reporter (e.g., conjugated gold beads) was added drop-wise to the entire strip such that the purplish liquid covered the strip. About 5 minutes were allowed to elapse and the positive control line became visible. The gold bead solution was carefully removed and saved for another strip. The strip was washed with wash buffer to minimize non-specific binding. The results were then read.

Assay Protocol: Test Strips with a Reporter

For strips that included a reporter (e.g., 80 nm gold particles conjugated with anti-GST antibodies, red latex beads conjugated with antibodies, etc.), strips were further prepared by placing a labeled conjugate pad below the first capture probe line (FIG. 5E; a "labeled conjugate pad" includes a reporter and is prepared by suspending the reporter in 30% sucrose and placing the solution (including the reporter) on a pad to dry overnight). An unlabeled pad (e.g., untreated glass fiber pad), referred to as a "sample pad," (e.g., 2 cm×1 cm) was placed below (i.e., prior to), but slightly overlapping with, the labeled conjugate pad (FIG. 5F; the sample pad allows an added sample to evenly enter the labeled conjugate pad).

50 µl of sample was mixed with 50 µl of dilution buffer (2×PBS with 2% ethanol, 2 ng/µl GST-His and 1% Tween 20). 75-100 µl of the mixture was added to the sample pad. The entire solution was allowed to wick across the test strip and into the absorbent pad (approximately 4 minutes). When the solution reached the absorbent pad, 75-100 µl wash buffer was added to the sample pad and allowed to wick across to the absorbent pad (approximately 4 minutes). The results were then read.

Results

Example 1

Figure 6:
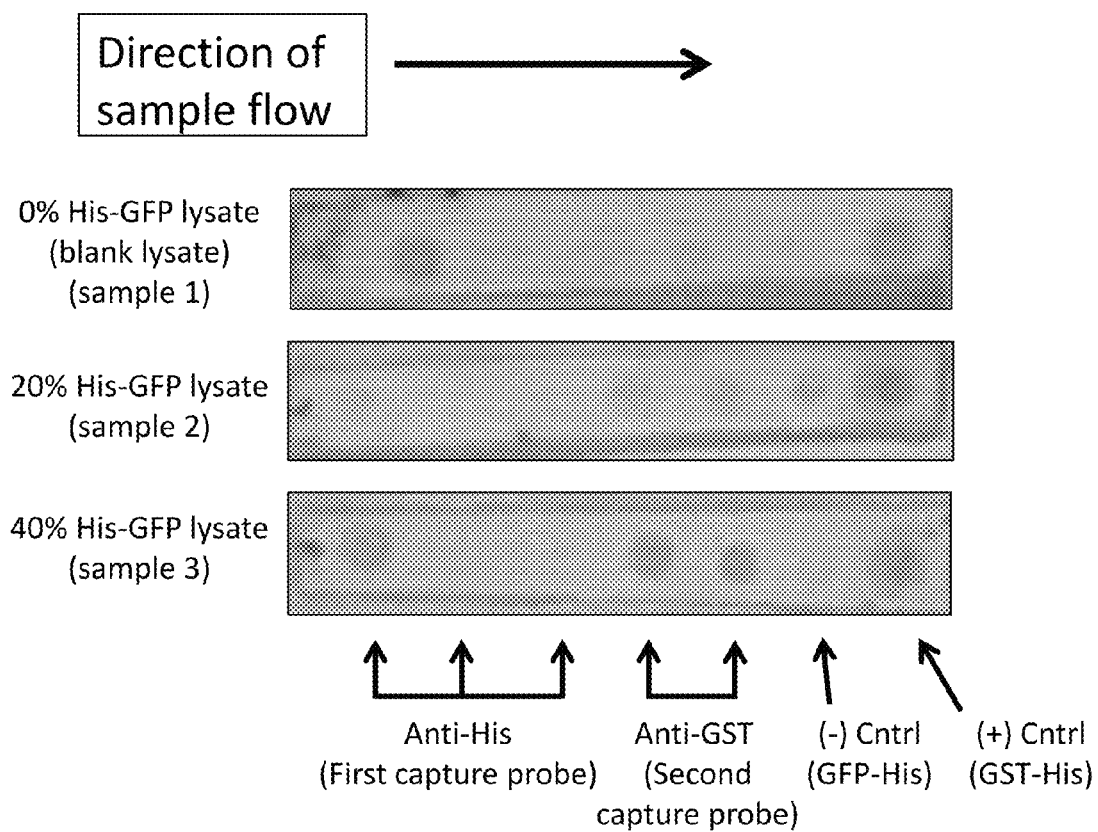
FIG. 6 Results from an exemplary assay. Samples 1-3 included 0%, 20%, or 40% His-GFP fusion protein lysate (the remainder was blank lysate), respectively. The competitor included a GST-His fusion protein. The first capture probe was an anti-His antibody. The second capture probe was an anti-GST antibody. The reporter included 80 nm gold beads conjugated to anti-GST antibodies. The negative control spot "(−) cntrl" was a GFP-His fusion protein pre-adsorbed onto the nitrocellulose test strip. The positive control spot "(+) cntrl" was a GST-His fusion protein pre-adsorbed onto the nitrocellulose test strip.

Samples were pre-mixed with competitor and added to test strip to wick across from left to right (FIG. 6). Samples (including the competitor, a GST-His fusion protein) therefore encountered a first capture probe (anti-His antibody) and then a second capture probe (anti-GST antibody). A negative control protein (GFP-His fusion protein) and a positive control protein (GST-His fusion protein) were pre-spotted (pre-adsorbed) onto the nitrocellulose test strip. Detection was accomplished by probing with a reporter (80 nm gold beads conjugated to anti-GST antibodies). Sample 1 (blank lysate): included no His-GFP fusion protein and was composed entirely of blank lysate. Sample 2: 20% was made up of His-GFP lysate and the remaining 80% was made up of blank lysate. Sample 3: 40% was made up of His-GFP lysate and the remaining 60% was made up of blank lysate. A positive signal was detected at the second capture probe only for samples that included the His-GFP fusion and the sample 3 exhibited a stronger signal than the sample 2, as expected. Because the assay is a competition-based assay and the reporter is an anti-GST antibody, the negative control (GFP-His fusion protein) was not detected and the positive control (GST-His fusion protein) was detected in all cases.

Example 2

Figure 7:
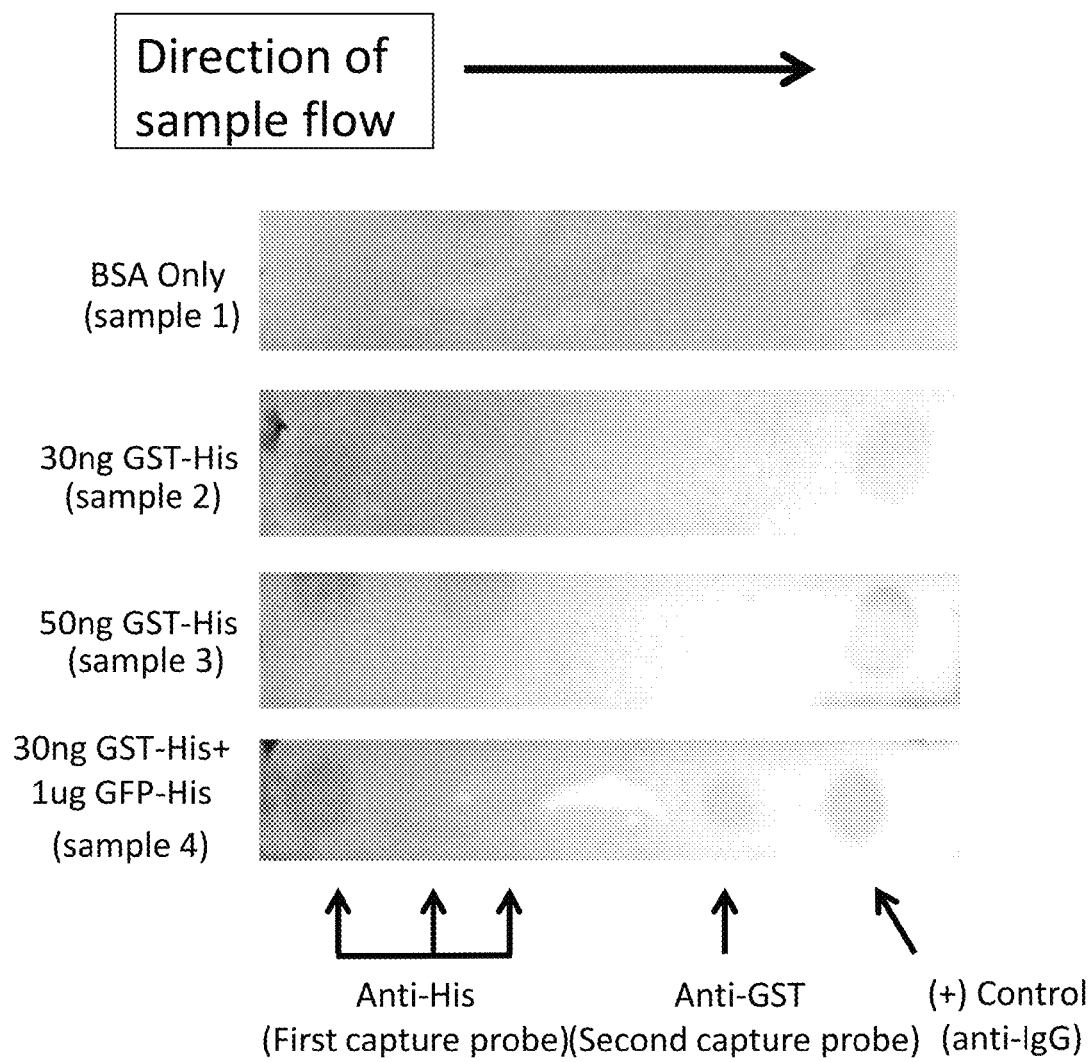
FIG. 7 Results from an exemplary assay. Sample 1: BSA only; Sample 2: 30 ng competitor; Sample 3: 50 ng competitor; Sample 4: 30 ng competitor plus 1 ug GFP-His fusion protein. The competitor included a GST-His fusion protein. The first capture probe was an anti-His antibody. The second capture probe was an anti-GST antibody. The immobilized control agent "(+) control" included an immobilized anti-IgG antibody. The reporter included red-colored latex beads conjugated to anti-GST antibodies.

Samples were pre-mixed with varying amounts of competitor (a GST-His fusion protein) and added to test strip to wick across from left to right (FIG. 7). Sample 1: BSA only; Sample 2: 30 ng competitor; Sample 3: 50 ng competitor; Sample 4: 30 ng competitor plus 1 ug GFP-His fusion protein. Samples encountered a first capture probe (anti-His antibody), a second capture probe (anti-GST antibody), and an immobilized control agent (anti-IgG antibody, i.e., "(+) control"). Detection was accomplished by probing with a reporter (red-colored latex beads conjugated to anti-GST antibodies). A positive signal was detected at the second capture probe only for the sample that included the GFP-His fusion protein (sample 4). Because the reporter is an IgG antibody (anti-GST antibody), a positive signal was detected in all four cases for the anti-IgG positive control immobilized control agent.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of determining whether an analyte is present in a sample, the method comprising:
   (a) providing a sample-contacted sample receiving region of a test lateral flow assay device, wherein the sample-contacted sample receiving region comprises:
      (i) a quantity of the sample;
      (ii) an immobilized first capture probe that specifically binds to the analyte; and
      (iii) a competitor comprising a first binding pair member that specifically binds to the first capture probe; and
   (b) reading a detection region of the test lateral flow assay device to determine whether the analyte is present in the sample, wherein the detection region comprises an immobilized detection capture probe that specifically binds to the competitor.

2. The method according to claim 1, wherein the sample-contacted sample receiving region is provided by combining the sample with the competitor prior to applying the sample to the sample receiving region.

3. The method according to claim 1, wherein the sample-contacted sample receiving region is provided by applying the competitor to the sample receiving region prior to applying the sample to the sample receiving region.

4. The method according to claim 1, wherein the sample-contacted sample receiving region is provided by applying the sample to the sample receiving region prior to applying the competitor to the sample receiving region.

5. The method according to claim 1, wherein the sample receiving region comprises the competitor.

6. The method according to claim 1, wherein the competitor further comprises a second binding pair member that specifically binds to the detection capture probe.

7. The method according to claim 1, wherein the competitor further comprises a label moiety.

8. The method according to claim 1, wherein the test lateral flow assay device further comprises an internal control region downstream from the detection region.

9. The method according to claim 1, wherein the sample-contacted sample receiving region of the test lateral flow assay device further comprises a reporter that specifically binds to the competitor.

10. The method according to claim 1, wherein the first binding pair member is a tag and the analyte is a tagged analyte.

11. The method according to claim 10, the method further comprising: producing the sample comprising the tagged analyte.

12. The method according to claim 1, the method further comprising:
   applying a control sample to a sample receiving region of a control lateral flow assay device; and
   reading a detection region of the control lateral flow assay device, wherein the control lateral flow assay device is identical to the test lateral flow assay device.

* * * * *